United States Patent [19]

Evans et al.

[11] Patent Number: 5,247,105
[45] Date of Patent: Sep. 21, 1993

[54] FATTY ACID HALOGENIDE MANUFACTURE

[75] Inventors: Reginald D. O. Evans, Merseyside, England; Raymond Jennings, Western Springs, Ill.

[73] Assignee: Unilever Patent Holdings B.V., Rotterdam, Netherlands

[21] Appl. No.: 659,973

[22] Filed: Feb. 26, 1991

Related U.S. Application Data

[63] Continuation-in-part of Ser. No. 515,759, Apr. 30, 1990, abandoned.

[30] Foreign Application Priority Data

Dec. 22, 1989 [EP] European Pat. Off. ........ 89313533.5

[51] Int. Cl.$^5$ ............................................. C07C 51/100
[52] U.S. Cl. .................................... 554/151; 554/150; 554/154; 562/840; 562/856; 562/864
[58] Field of Search ................ 260/408; 554/150, 151, 554/154; 862/840, 856, 864

[56] References Cited

U.S. PATENT DOCUMENTS

| | | | |
|---|---|---|---|
| 3,149,155 | 9/1964 | Seefelder et al. | 260/544 |
| 3,318,950 | 5/1967 | Christoph, Jr. et al. | 260/408 |
| 4,900,479 | 2/1990 | Frendenberg et al. | 260/408 |

FOREIGN PATENT DOCUMENTS 0031504  7/1981  European Pat. Off. .

OTHER PUBLICATIONS

Chemical Abstracts, vol. 67, p. 9384; 99872d, 1967.
Patent Abstracts of Japan, vol. 5, No. 184 (C-80)[856], Nov. 21, 1981.

*Primary Examiner*—José G. Dees
*Assistant Examiner*—Deborah D. Carr
*Attorney, Agent, or Firm*—Cushman, Darby & Cushman

[57] ABSTRACT

The invention provides a process for preparing fatty acid halide by reacting a fatty acid with a halogenating agent optionally followed by hydrolysis of unreacted halogenating agent and separating the fatty acid halide upper layer from the inorganic lower layer characterized in that a fatty acid nitrogen derivative, preferably a fatty amide has been incorporated in the reaction mixture. Preferably the fatty acid is a saturated or unsaturated $C_6$ to $C_{24}$ fatty acid and the halogenating agent a phosphorus halide, especially phosphorus trichloride.

11 Claims, No Drawings

FATTY ACID HALOGENIDE MANUFACTURE

This application is a continuation-in-part of co-pending application Ser. No. 515,759 filed Apr. 30, 1990, now abandoned.

This invention relates to an improved process for the manufacture of fatty acid halides (halogenides), more in particular fatty acid chlorides. Fatty acid halogenides, in particular fatty acid chlorides are valuable commercially available compounds often used as in the manufacture of acyl taurides and certain esters and also in the manufacture of alkyl ketene dimers (AKD) used in paper sizing.

Traditionally acid chlorides have been prepared by reaction of fatty acid with chlorinating agents like phosphorus trichloride, phosphorus pentachloride or thionylchloride followed by separation of the fatty acid halogenide obtained from the inorganic material.

It is known from DE-A- 1 280 854 (VEB Leuna-Werke "Walter Ulbricht") to react fatty acid with excess phosphorus trichloride in one or more reactors at a temperature between 40° and 80° C. and a residence time of 10 to 140 minutes and to transfer the reaction product to a separation vessel where the upper fatty acid chloride layer is separated from the lower phosphorous acid layer. The upper fatty acid chloride layer also contains unreacted phosphorus trichloride.

According to U.S. Pat. No. 2,262,431 (Armour & Co) after the reaction between fatty acid and phosphorus halide any unreacted phosphorus halide can be hydrolyzed with water to form phosphoric acid or phosphorous acid without affecting the fatty acid halide so that a substantially pure fatty halide upper layer can be obtained.

When preparing fatty acid halides on a commercial scale one of the problems encountered is the separation of the fatty acid halide from the inorganic material because the settling into two layers is often difficult and time consuming inter alia because of a emulsification taking place.

What is needed for practical scale operations is quick separation and clarification with a clean interface before the lower inorganic layer can be removed efficiently that is within 6, preferably within 3 hours.

The invention therefore provides a method for preparing fatty acid halide by reacting a fatty acid with a halogenating agent optionally followed by hydrolysis of unreacted halogenating agent and separating the fatty acid halide upper layer from the inorganic lower layer by incorporating in the reaction mixture a fatty acid nitrogen derivative.

We are aware of U.S. Pat. No. 4,900,479 (Freudenberg/BASF) which describes a process carried out in the presence of at least 0.5 mole % a carboxyamide, such as dimethylformamide hydrochloride. The present invention differs in that a fatty acid nitrogen derivative is used.

Certain low grade fatty acids, prepared for instance from crude tallow contain small amounts of fatty acid amine together with many other impurities like amides, alcohols, alkanes, colour bodies etc. Of course no good quality fatty acid halides can be prepared from such low grade fatty acids. The present invention therefore aims especially at the preparation of high quality fatty acid halide i.e. those containing less than 0.5% (w.w.), preferably less than 0.3% of unsaponifiable material and consequently also the fatty acid starting materials should have a similar degree of purity.

In accordance with the present invention the process employs a saturated or unsaturated $C_2$ to $C_{24}$, especially a $C_{12}$ to $C_{24}$, fatty acid as starting material and obtains fatty halides of the same chain length.

In a preferred embodiment of the invention the halogenating agent used is a phosphorus halide, preferably phosphorus trichloride.

It is further preferred to incorporate in the reaction mixture from 0.01 to 0.5, more preferably from 0.05 to 0.2% (w.w.) of the fatty acid nitrogen derivative calculated on the fatty acid starting material. The fatty acid nitrogen derivative will be soluble in the fatty acid at these concentrations. The fatty acid nitrogen derivative may be selected from fatty nitriles, primary, secondary or tertiary amines, diamines, quaternary ammonium salts, fatty amine oxides, mono- or di-substituted fatty amides and the like. It is recommended to use as the fatty amide such a compound containing from 2 to 44, preferably 10 to 36 carbon atoms, especially a primary amide containing 4 to 24, preferably from 12 to 24 carbon atoms or alternatively a secondary amide containing 24 to 44 carbon atoms. Similar chain length considerations also apply to the fatty amine, and to other fatty acid nitrogen derivatives, when used.

From the point of view of processing it is advantageous to add the fatty acid nitrogen derivative to fatty acid prior to the reaction with the halogenating agent.

It is preferred that the reaction of the fatty acid with the halogenating agent is carried out in one or more reactors at a temperature between 40° and 70° C. and a residence time of 10 to 140. The reaction product is preferably subsequently transferred to a separation vessel where the upper fatty acid halide layer is separated from the lower inorganic layer.

The phosphorus halide is preferably used in molar excess over the fatty acid. After the reaction between fatty acid and phosphorus halide any unreacted phosphorus halide can be hydrolyzed with water to form phosphoric acid or phosphorous acid without affecting the fatty acid halide, so that a substantially pure fatty acid halide upper layer can be obtained. The settling of the reaction mixture into two layers is considerably facilitated according to the present invention and a clean interface is usually obtained, with a clear to slightly cloudy upper layer. This invention therefore leads to a higher throughput in the existing equipment. The inorganic lower layer is then separated and a substantially pure fatty acid halide obtained. Also the invention permits the preparation of fatty acid halides from pure starting materials containing from 0.1 to 0.3% of unsaponifiable material with a good and rapid phase separation.

EXAMPLES

Fatty acids are heated to 65°-70° C. with stirring. Phosphorus trichloride (1.5 molar excess calculated on the fatty acids) was added over a period of 15 minutes. After addition the reaction mixture was stirred for a further 30 minutes. The mixture was then allowed to settle at the reaction temperature.

The upper layer was slightly cloudy. The separation/clarification point was defined as when the upper phase of acid chloride is completely clear with a clean interface.

The results are tabulated below.

| Fatty acid starting material | Clearance time (hrs) | | | Additive |
|---|---|---|---|---|
| | No additive | additive | | |
| T6 (HCD + HD) Blend | 5 | 1.75 | (0.05%) | OM |
| T6 (HCD + HD) Blend | 3.5 | 2 | (0.05%) | OM |
| T6 (HCD) | 6.75 | 2.5 | (0.05%) | OM |
| T2 (HCD) | 4 | 3.25 | (0.1%) | OM |
| T6 (HCD + HD) Blend | 4 | 3 | (0.05%) | OM |
| T6 | 2.5 | 1.5 | (0.05%) | OM |
| T6 | 3.5 | 2.5 | (0.05%) | OM |
| T6 | 4 | 3 | (0.05%) | OM |
| T6 | 3.5 | 1.5 | (0.05%) | OM |
| T6 | 2.75 | 1.75 | (0.05%) | OM |
| T2 (HCD) | 6 | 3.25 | (0.1%) | X |
| T2 (HCD) | 6 | 1.25 | (0.2%) | X |

T2 and T6 stand for tallow fatty acids prepared from tallow 2 and tallow 6 respectively as defined in British standard 3919 (1987). OM stands for oleylamide and X stands for N-phenylethylstearamide. H stands for hydrogenated, C for crystallized from methanol and D for distilled starting fatty acids and they all contained from 0.1 to 0.2% (w.w.) of unsaponifiable material.

Similar beneficial results are obtained when the oleylamide is replaced with oleylamine or with stearylamine.

We claim:

1. In a process for preparing a fatty acid halide by reacting a fatty acid with a halogenating agent and allowing phase separation to occur to provide an upper organic layer containing the fatty acid halide with a lower inorganic layer, and then separating the fatty acid halide upper layer from the inorganic lower layer, the improvement which comprises carrying out the reaction between the fatty acid and the halogenating agent in the presence of a small but effective amount of fatty acid nitrogen derivative in the reaction mixture, said derivative being present in an amount sufficient to facilitate phase separation of the upper and lower layers.

2. A process according to claim 1 wherein the fatty acid is a saturated or unsaturated $C_2$ to $C_{24}$ fatty acid.

3. A process according to claim 1 wherein the halogenating agent is a phosphorus halide.

4. A process according to claim 1 in which the fatty acid nitrogen derivative is added to the fatty acid prior to the reaction with the halogenating agent.

5. A process according to claim 1 in which the fatty acid starting material contains less than 0.5% by weight of unsaponifiable material.

6. A process according to claim 1 in which 0.02 to 0.5 by weight of the fatty acid nitrogen derivative (calculated on the fatty acid) is incorporated in the reaction mixture.

7. A process according to claim 1, wherein the fatty acid nitrogen derivative is selected from fatty nitriles, primary, secondary or tertiary amines, diamines, quaternary ammonium salts, fatty amine oxides and mono- or di- substituted fatty amides.

8. A process according to claim 1 in which the fatty acid nitrogen derivative is a fatty amide which contains from 2 to 44 carbon atoms.

9. A process according to claim 8 in which the fatty amide is a primary amide.

10. A process according to claim 8 in which the amide is a secondary amide.

11. A process according to claim 1 wherein the fatty acid nitrogen derivative contains from 10 to 44 carbon atoms.

* * * * *